US00PP11913P2

(12) United States Plant Patent
Glicenstein

(10) Patent No.: US PP11,913 P2
(45) Date of Patent: Jun. 5, 2001

(54) AZALEA PLANT NAMED 'FIRST PLACE'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/498,709

(22) Filed: Feb. 7, 2000

(51) Int. Cl.[7] ..... A01H 5/00
(52) U.S. Cl. ..... Plt./240
(58) Field of Search ..... Plt./238, 239, 240

*Primary Examiner*—Bruce Campell
*Assistant Examiner*—Kent L. Bell

(74) *Attorney, Agent, or Firm*—C. A. Whealy

(57) ABSTRACT

A new and distinct cultivar of Azalea plant named 'First Place', characterized by its very glossy dark green leaves that do not abscise during the cooling and forcing periods; dense and outwardly spreading plant habit; vigorous growth habit; freely branching habit; rapid flowering after forcing; numerous large and showy reddish purple-colored flowers; hose-in-hose to semi-double hose-in-hose flower form; excellent postproduction longevity with plants maintaining good flower substance for more than four weeks in an interior environment; and very low incidence of infection with Cylindrocladium in inoculated trials.

2 Drawing Sheets

BACKGROUND OF THE INVENTION

The present Invention relates to a new and distinct cultivar of Azalea, botanically known as *Rhododendron hybrida*, an evergreen greenhouse-forcing type Azalea, and hereinafter referred to by the name 'First Place'.

The new Azalea is a product of a planned breeding program conducted by the Inventor in Alva, Fla. The objective of the breeding program is to create new Azalea varieties having uniform plant habit and uniform flowering, numerous flowers, dark green foliage, good foliage retention during the cooling and forcing periods, resistance to Cylindrocladium, and excellent postproduction longevity.

The new Azalea originated from a cross made by the Inventor in Alva, Fla., of the commercial cultivar 'Prize', disclosed in U.S. Plant Pat. No. 3,795, as the female, or seed, parent with the nonpatented commercial cultivar 'Gloria' as the male, or pollen, parent.

Compared to plants of the female parent, the cultivar 'Prize', plants of the new Azalea are slightly more vigorous; more outwardly spreading; have glossier, broader and darker green leaves; are more freely flowering; have slightly redder (less blue) flower color, have better flower color retention, and are more resistant to Cylindrocladium in inoculation trials. Compared to plants of the male parent, the cultivar 'Gloria', plants of the new Azalea differ in flower color; flower about five days earlier after cooling; are less susceptible to amide injury (foliar burn); have better foliage retention; and have longer post-production longevity.

The new Azalea was discovered and selected by the Inventor as a flowering plant within the progeny of the stated cross in a controlled environment in Alva, Fla., in May, 1993. The selection of this plant was based on its desirable flower color, profuse and uniform flowering, improved flower color retention, excellent postproduction longevity, and resistance to Cylindrocladium.

Asexual reproduction of the new Azalea by terminal cuttings taken in a controlled environment in Alva, Fla., has shown that the unique features of this new Azalea are stable and reproduced true to type in successive generations.

SUMMARY OF THE INVENTION

The new Azalea has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'First Place'. These characteristics in combination distinguish 'First Place' as a new and distinct cultivar:

1. Very glossy dark green leaves that do not abscise during the cooling and forcing periods.
2. Dense and outwardly spreading plant habit; vigorous growth habit.
3. Very freely branching.
4. Rapid flowering after forcing.
5. Numerous large and showy reddish purple-colored flowers.
6. Hose-in-hose to semi-double hose-in-hose flower form.
7. Flowers that do not shatter.
8. Good flower color retention even under high light.
9. Excellent postproduction longevity with plants maintaining good flower substance for more than four weeks in an interior environment.
10. Very low incidence of infection with Cylindrocladium in inoculated trials.

BRIEF DESCRIPTION OF THE PHOTOGRAPHS

The accompanying colored photographs illustrate the overall appearance of the new Azalea. These photographs show the colors as true as it is reasonably possible to obtain in colored reproductions of this type. Colors in the photographs may differ slightly from the color values cited in the detailed botanical description, which accurately describe the actual colors of the new Azalea.

The photograph on the first sheet comprises a top perspective view of a typical plant of 'First Place'.

The photograph at the top of the second sheet is a close-up view of typical flowers of 'First Place'.

The photograph at the bottom of the second sheet comprises a close-up view of typical flowers of 'First Place' (left) and 'Prize' (right).

DETAILED BOTANICAL DESCRIPTION

The aforementioned and following observations, measurements, values, and comparisons describe plants grown in Alva, Fla., in 12.5-cm containers with day temperatures ranging from 16 to 35° C. and night temperatures ranging from 10 to 24° C. Plants were grown under 50 percent polypropylene shade cloth reducing ambient light levels to about 4,000 to 5,000 footcandles. Plants used for the description and photographs were about 12 months from planting. After flower bud development, plants were cooled at 3 to 5° C. for six weeks to break flower bud dormancy. Plants were subsequently forced into flower under commercial conditions in a polyethylene-covered greenhouse.

In the following description, color references are made to The Royal Horticultural Society Colour Chart except where general terms of ordinary dictionary significance are used.

Botanical classification:

*Botanical.*—*Rhododendron hybrida* 'First Place'.

*Commercial.*—Evergreen greenhouse-forcing type Azalea.

Parentage:

*Female or seed parent.*—Commercial *Rhododendron hybrida* cultivar 'Prize', disclosed in U.S. Plant Pat. No. 3,795.

*Male or pollen parent.*—Commercial *Rhododendron hybrida* cultivar 'Gloria', not patented.

Propagation:

*Type.*—By terminal cuttings.

*Time to initiate roots.*—Summer: About 35 days at temperatures of 24° C. Winter: About 42 days at temperatures of 24° C.

*Time to develop roots.*—Summer: About 63 days at temperatures of 24° C. Winter: About 77 days at temperatures of 24° C.

*Root description.*—Vigorous; finely-branched.

Plant description:

*Plant form and growth habit.*—Perennial, evergreen; outwardly spreading plant habit; inverted triangle; vigorous growth habit. Densely foliated. Freely flowering; numerous flowers per plant.

*Branching habit.*—Very freely branching; about four or five lateral branches develop after removal of terminal apex.

*Plant height, soil level to top of flowers.*—About 29 cm.

*Plant diameter, area of spread.*—About 51 cm.

*Lateral branch description.*—Length: About 26.5 cm. Diameter at base: About 6 mm. Color: Immature: Between 144A and 144B. Mature: Woody, between 165A and 165B. Texture: Sparsely pubescent.

Foliage description:

*Arrangement.*—Alternate, single.

*Length.*—About 4.2 cm.

*Width.*—About 2.7 cm.

*Shape.*—Elliptic to obovate.

*Apex.*—Mucronate.

*Base.*—Attenuate.

*Margin.*—Entire.

*Texture.*—Leathery; very sparse pubescence on upper surface.

*Color.*—Young foliage, upper surface: Very glossy; darker than 147A. Young foliage, lower surface: Close to 147B. Mature foliage, upper surface: Very glossy; much darker than 147A. Mature foliage, lower surface: Close to 147B.

*Petiole.*—Length: About 7 mm. Diameter: About 2 mm. Color: 144A to 144B.

Flower description:

*Natural flowering season.*—Spring after sufficient cool period.

*Flower arrangement.*—Flowers arranged singly at terminals with usually about three flowers per apex. Flowers face upward and outward. Very freely flowering. Not fragrant.

*Flower appearance.*—Large-sized star-shaped hose-in-hose flower form. Reddish purple-colored petals. Flowers persistent.

*Flower diameter.*—About 7.5 cm.

*Flower depth.*—About 3.25 cm.

*Postproduction longevity.*—Under interior conditions, plants maintain good flower substance for more than four weeks.

*Flower bud* (*just starting to show petal color*).—Rate of opening: About three to four days depending on temperatures. Length: About 1.25 cm. Diameter: About 6 mm. Shape: Ovoid, elongated. Color: 60A.

*Petals.*—Arrangement: Hose-in-hose flower form; single whorl of five fused petals surrounded by whorl of sepals transformed into a complete whorl of petals. One or two stamens may be transformed into petals; making the flower form semi-double hose-in-hose. Length: About 3.8 cm. Width: About 2.9 cm. Shape: Roughly elliptic with rounded apex. Margin: Entire; undulating. Texture: Smooth, velvety. Color: When opening, upper surface: Close to 60A to 61B to 63A. When opening, lower surface: Close to 60A to 61B to 63A. Fully opened, upper surface: Close to 60B to 60C to 61B to 63A; spots, 60A. Fully opened, lower surface: Close to 61B to 63A. Throat: Close to 63A to darker than 63B.

*Sepals.*—Arrangement: Single whorl of five fused petal-like sepals. Length: About 3.7 cm. Width: About 2.8 cm. Shape: Roughly elliptic with rounded apex. Margin: Entire, undulating. Texture: Smooth, velvety. Color: Upper surface: Close to 60B to 60C to 61B to 63A. Lower surface: Close to 61B to 63A.

*Peduncles.*—Length: About 1.8 cm. Diameter: About 1.75 mm. Angle: Upright. Strength: Flexible, strong. Texture: Very pubescent. Color: 144A.

*Reproductive organs.*—Androecium: Stamens: Typically five or seven; one or two stamens may be transformed into petals. Anther shape: Oblong. Anther size: About 3 mm by 1 mm. Anther color: Close to 167A. Amount of pollen: None observed. Gynoecium: Pistil number: One. Pistil length: About 2.8 cm. Stigma shape: Rounded. Stigma color: Light tan. Style length: About 2.5 mm. Style color: 63A. Ovary color: 63A; heavily whiskered.

Disease resistance: Very low incidence of infection by *Cylindrocladium* in inoculated trials; trials repeated in Alva, Fla., during the summers of 1997, 1998 and 1999.

Seed production: Seed production has not been observed.

It is claimed:

1. A new and distinct Azalea plant named 'First Place', as illustrated and described.

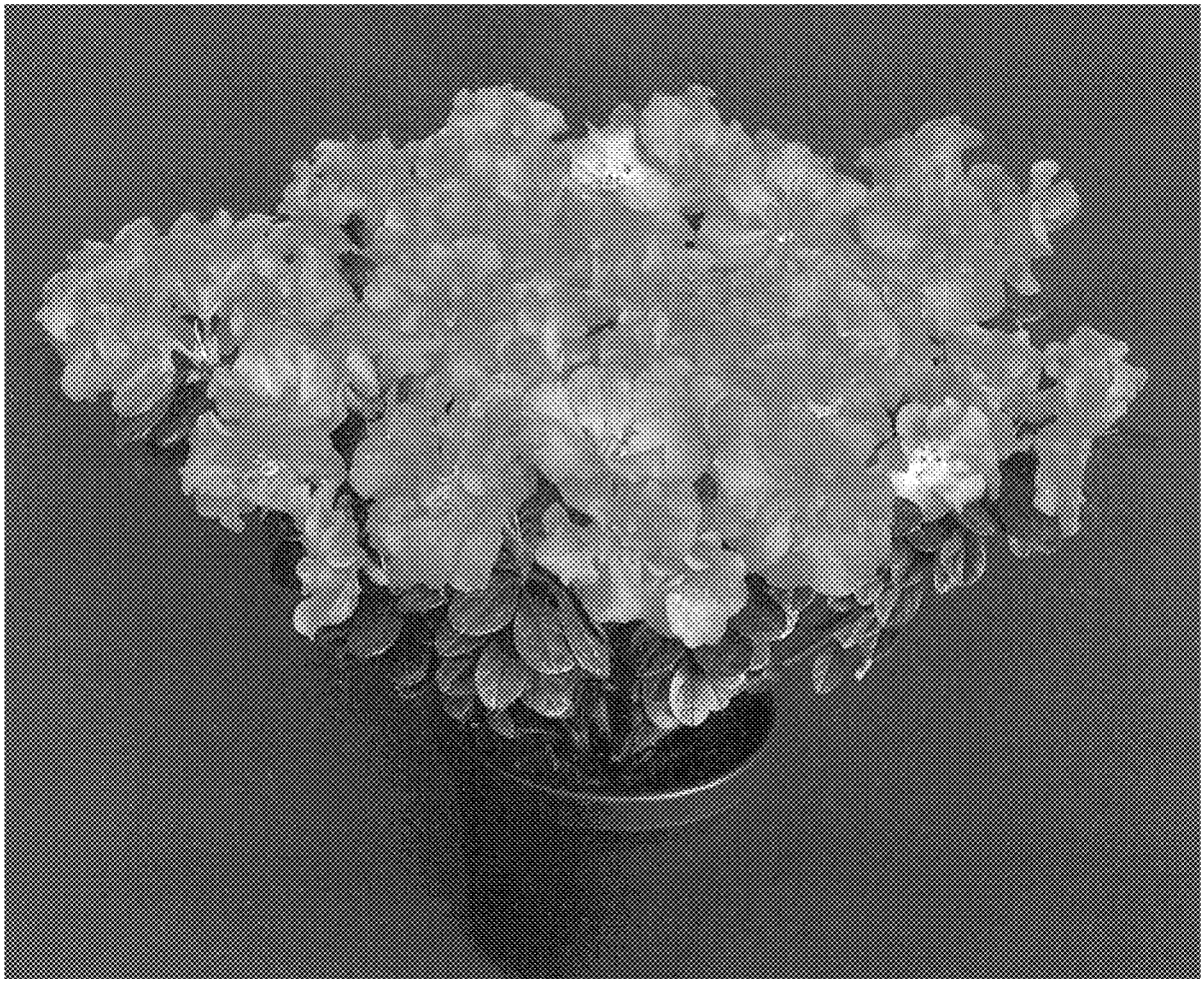

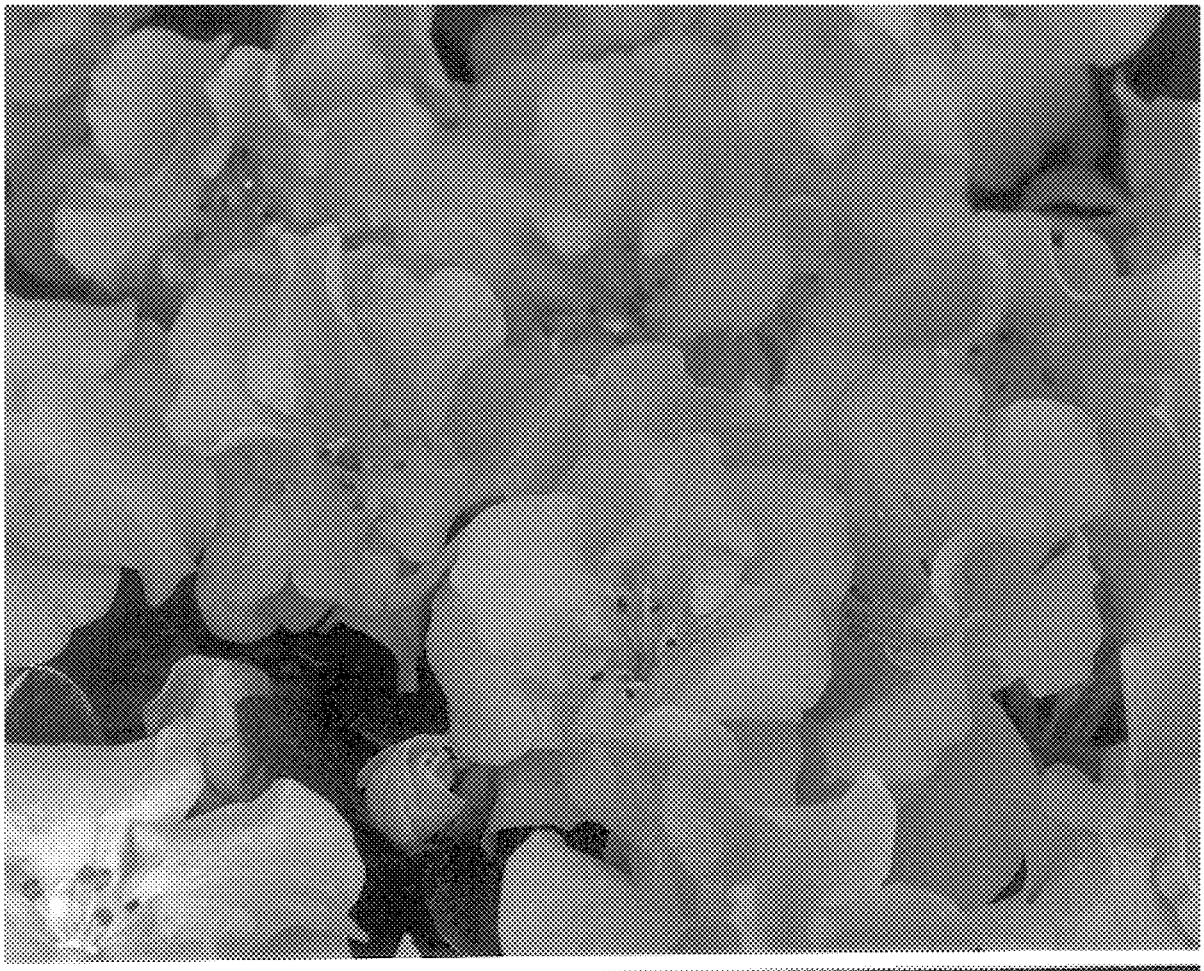
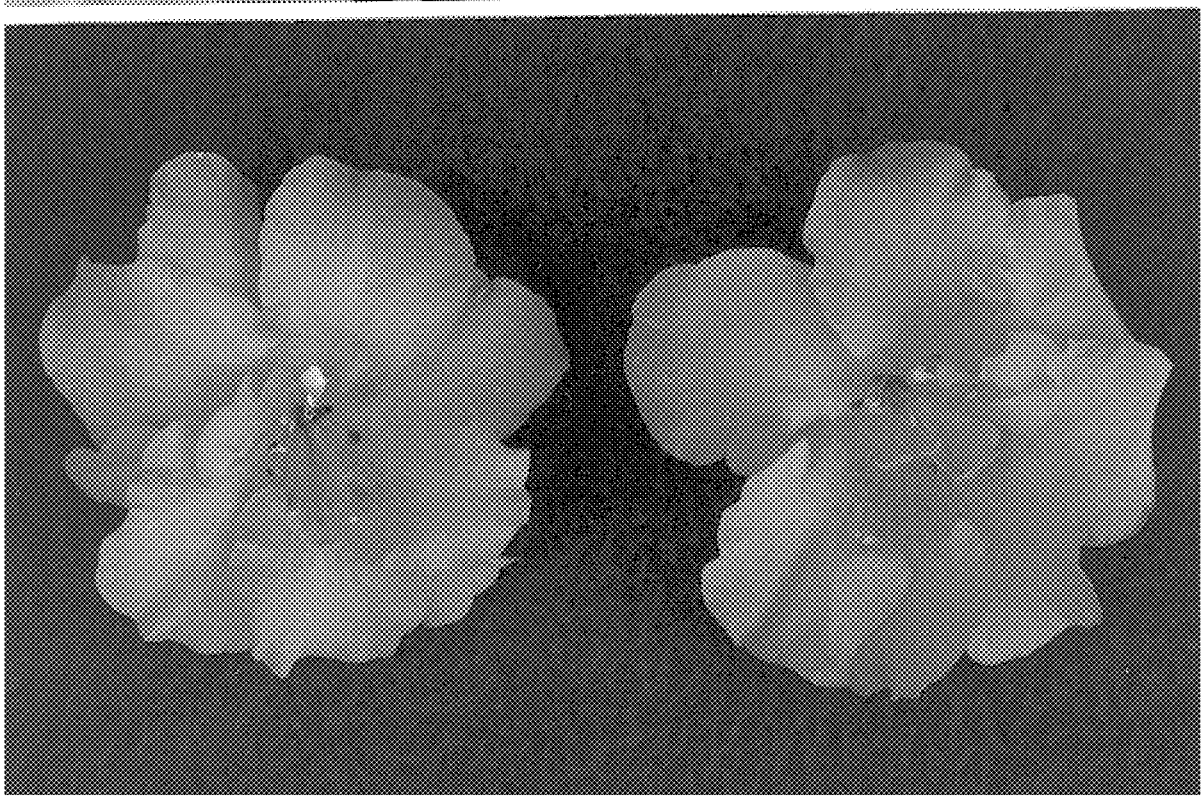

* * * * *